United States Patent [19]

Kusaba et al.

[11] Patent Number: 4,918,089
[45] Date of Patent: Apr. 17, 1990

[54] AMIDE DERIVATIVES, AND THEIR PRODUCTION AND AGRICULTURAL FUNGICIDES CONTAINING THEM

[75] Inventors: Tomoyuki Kusaba, Toyonaka; Kazue Shinsugi, Kobe; Tsuguhiro Katoh; Naoto Meki, both of Toyonaka; Masayo Sugano, Osaka; Tomohiro Teramae, Takarazuka; Yukio Oguri, Toyonaka; Tamon Uematsu, Kobe, all of Japan

[73] Assignee: Sumitomo Chemical Company Limited, Osaka, Japan

[21] Appl. No.: 396,818

[22] Filed: Aug. 22, 1989

Related U.S. Application Data

[63] Continuation of Ser. No. 198,283, May 25, 1988, abandoned.

[30] Foreign Application Priority Data

May 26, 1987 [JP] Japan .................... 62-130392
Feb. 3, 1988 [JP] Japan .................... 63-024524
Mar. 23, 1988 [JP] Japan .................... 63-070191

[51] Int. Cl.$^4$ .................... C07D 417/12; A01N 43/78
[52] U.S. Cl. .................... 514/365; 548/200
[58] Field of Search .................... 548/200; 514/365

[56] References Cited

U.S. PATENT DOCUMENTS

| | | | |
|---|---|---|---|
| 4,432,784 | 2/1984 | Kay et al. ............... | 548/200 |
| 4,506,084 | 3/1985 | Kay et al. ............... | 548/200 |
| 4,515,959 | 5/1985 | Kay et al. ............... | 548/200 |
| 4,552,887 | 11/1985 | Kay et al. ............... | 548/200 |
| 4,792,565 | 12/1988 | Shimotori ............... | 514/406 |

FOREIGN PATENT DOCUMENTS

| | | | |
|---|---|---|---|
| 0061836 | 2/1982 | European Pat. Off. ........... | 548/200 |
| 0076030 | 8/1982 | European Pat. Off. ........... | 548/200 |
| 268892 | 6/1988 | European Pat. Off. ........... | 548/200 |
| 292937 | 11/1988 | European Pat. Off. ........... | 548/200 |
| 313091 | 4/1989 | European Pat. Off. ........... | 548/200 |
| 1211889 | 11/1967 | United Kingdom ............... | 548/200 |

OTHER PUBLICATIONS

Hantzsch, A., Annalen der Chemie 250, pp. 257–273, (1889).
Boon, W. R., J. Chem. Soc., pp. 601–603 (1945).
Abstract of JP-A-103067/1987.
Krohnke et al., Angew Chem., 73, Jahrg., 1961, Nr. 1.

*Primary Examiner*—Robert Gerstl
*Attorney, Agent, or Firm*—Birch, Stewart, Kolasch & Birch

[57] ABSTRACT

An amide compound of the formula:

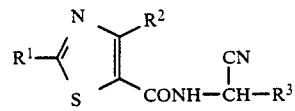

wherein $R^1$ and $R^2$ are, the same or different, each a hydrogen atom or a $C_1$–$C_3$ alkyl group and $R^3$ is a 2-furyl group, a 3-furyl group, a 2-thienyl group or a 3-thienyl group, which is useful as an agricultural fungicide.

13 Claims, No Drawings

AMIDE DERIVATIVES, AND THEIR PRODUCTION AND AGRICULTURAL FUNGICIDES CONTAINING THEM

This application is a continuation, of application Ser. No. 07/198,283 filed on May 25, 1988, now abandoned.

The present invention relates to novel amide derivatives, and their production and an agricultural fungicide containing them.

As the prevalent agricultural fungicides for controlling plant diseases caused by phytopathogenic fungi such as Pythiaceae and Peronosporaceae, there are known captan, captafol, dithiocarbamates, etc. However, almost all of them show a preventive effect, and a curative effect is hardly produced thereby. Such fungicidal activity is not sufficient to control plant diseases when applied after germination of phytopathogenic fungi. This is disadvantageous, because application of fungicides after slight germination of phytopathogenic fungi is sometimes required depending on the circumstances. Therefore, there is always a strong demand for a fungicide exerting a high preventive effect and an excellent systemic activity so as to produce a curative effect. This is particularly true for controlling plant diseases showing rapid development of symptoms, for instance, caused by Peronosporales. Recently, there was provided metalaxyl (i.e. N-(2,6-dimethylphenyl)-N-(methoxyacetyl)alanine methyl ester) having an excellent systemic activity and showing a good curative effect. Since, however, organisms resistant to metalaxyl appeared shortly after its commercialization, its curative effect could not be fully appreciated. Under the above circumstances, the appearance of a new fungicide having an excellent systemic activity and showing a prominent curative effect, particularly of the one effectively applicable to downy mildew of grapes, has been highly demanded in the world.

As a result of an extensive study, it has now been found that amide compounds of the formula:

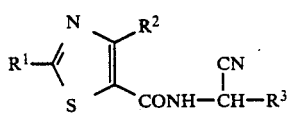
(I)

wherein $R^1$ and $R^2$ are, the same or different, each a hydrogen atom or a $C_1$-$C_3$ alkyl group and $R^3$ is a 2-furyl group, a 3-furyl group, a 2-thienyl group or a 3-thienyl group have a strong antifungal activity with an excellent systemic activity and a curative effect without phytotoxicity.

Among the amide compounds (I), preferred are those of the formula:

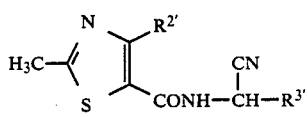
(I-1)

wherein $R^{2'}$ is a methyl group or an ethyl group and $R^{3'}$ is a 2-thienyl group or a 3-thienyl group.

Particularly preferred are those of the formula:

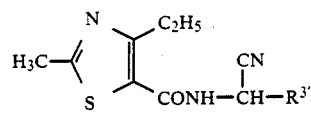
(I-2)

wherein $R^{3'}$ is as defined above.

There have been known a great number of amide compounds which are useful as fungicides and/or herbicides. Among them, similar to the amide compounds (I) in chemical structure are the compounds of the formula (I) wherein the thiazole ring is substituted with a substituted benzene, furan, thiophene, benzofuran or pyridine ring as disclosed in U.S. Pat. No. 4,432,784, the compounds of the formula (I) wherein the thiazole ring is substituted with a substituted benzene, furan or thiophene ring as disclosed in U.S. Pat. Nos. 4,515,959 and 4,552,887; the compounds of the formula (I) wherein the thiazole ring is substituted with a 4-substituted benzene ring as disclosed in EP-A-0174088, the compounds of the formula (I) wherein the thiazole ring is substituted with an alkyl, alkenyl, alkoxyalkyl, cycloalkyl, haloalkyl or haloalkenyl group as disclosed in JA-A-103067/1987, etc. However, these known compounds are not sufficient in terms of efficacy on plant diseases, particularly diseases caused by phytopathogenic fungi such as Peronosporales (e.g. downy mildew, late bright) and also in systemic activity. In addition, their phytotoxicity is considerably strong. It may be thus stated that the remarkable preventive and curative effect of the amide compounds (I), especially compound (I-2), on plant diseases caused by phytopathogenic fungi without producing any material phytotoxicity is quite unexpected from the above mentioned known patents and literature.

The amide compounds (I) may be produced, for instance, by linking a carboxylic acid halide of the formula:

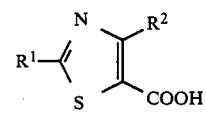
(II)

wherein $R^1$ and $R^2$ are each as defined above and an aminonitrile of the formula:

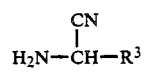
(III)

wherein $R^3$ is as defined above in their reactive forms. Some typical procedures for accomplishment of the above linking will be hereinafter explained in details.

Procedure (A):

According to this procedure, an acid halide of the formula:

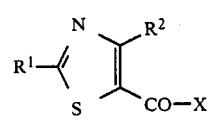
(IV)

wherein $R^1$ and $R^2$ are each as defined above and X is a halogen atom (e.g. chlorine, bromine) is reacted with the aminonitrile (III) or its salt to give the compound (I).

In general, the reaction is carried out at a temperature of about −30° to 50° C., preferably about 0° C. to room temperature, for a period of about 30 minutes to 24 hours, preferably about 1 to 8 hours, normally in the presence of a base. Examples of the base are tertiary amines (e.g. pyridine, 4-dimethylaminopyridine, triethylamine, N,N-dimethylaniline, tributylamine, N-methylmorpholine), inorganic bases (e.g. sodium hydroxide, potassium hydroxide, calcium carbonate, sodium hydride), etc. The aminonitrile (III) or its salt and the base may be employed respectively in amounts of about 1 to 2 equivalents and of about 1 to 3 equivalents to 1 equivalent of the acid halide (IV). The aminonitrile (III) itself may be also employed as the base. Any solvent may be used optionally in the reaction, and its examples include aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, ethylene glycol dimethyl ether), ketones (e.g. acetone, methyl ethyl ketone, methyl isobutyl ketone, isophorone, cyclohexanone), esters (e.g. ethyl formate, ethyl acetate, butyl acetate, diethyl carbonate), nitro compounds (e.g. nitromethane, nitrobenzene), nitriles (e.g. acetonitrile, isobutylnitrile), acid amides (e.g. formamide, N,N-dimethylformamide, N,N-dimethylacetamide), sulfur compounds (e.g. dimethylsulfoxide, sulfolane), etc. Water is also usable as the solvent insofar as any water-reactive inorganic base such as sodium hydride is not employed. The solvents may be used solely or in combination.

After completion of the reaction, the reaction mixture may be subjected to post-treatment in a per se conventional manner, for instance, by washing them with water, separating and concentrating the organic layer and optionally purifying the resulting product. For purification, chromatography or recrystallization may be adopted.

Procedure (B):

According to this procedure, the carboxylic acid (II) is reacted with an N,N'-thionyldiimidazole of the formula:

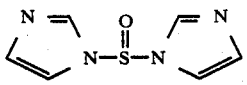

to give an acylimidazole of the formula:

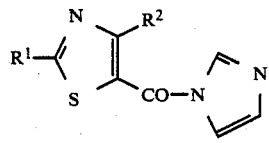

wherein $R^1$ and $R^2$ are each as defined above, and then the acylimidazole (VI) is reacted with the aminonitrile (III) or its salt to give the amide compound (I).

The reactions in the initial step and the subsequent step are normally carried out successively without isolation of the acylimidazole (VI), because it is usually not sufficiently stable. Those reactions may be carried out at a temperature of about −30° to 50° C., preferably 0° C. to room temperature, for a period of about 30 minutes to 24 hours, preferably about 1 to 8 hours. The proportion of the carboxylic acid (II), N,N'-thionyldiimidazole (V) and the aminonitrile (III) or its salt is usually about 1:1:1–2 in equivalent. Any solvent may be used optionally in the reaction, and examples of the solvent as usable are those as exemplified with respect to Procedure (A), but the use of water should be avoided.

After completion of the reaction, the reaction mixture may be subjected to post-treatment in a per se conventional manner, for instance, by washing them with water, separating and concentrating the organic layer and optionally purifying the resultant product. For purification, chromatography or recrystallization may be adopted.

In the above procedures, some of the carboxylic acid (II) and the acid halide (IV) are known, and some others may be produced according to the procedures as described in the literature. For instance, 2,4-disubstituted thiazole-5-carboxylic acids are disclosed in Ann., 250, 257 (1889) and 2,4-disubstituted thiazole-5-carbonyl chloride is disclosed in J. Chem. Soc., 601 (1945). Likewise, Angew. Chem., 73, 26 (1961) discloses the preparation method of the N,N'-thionyldiimidazole.

The aminonitrile (III) is readily obtainable by reacting the corresponding aldehyde with ammonia and potassium or sodium cyanide according to the Strecker reaction.

The amide compounds (I) of the invention have one asymmetric carbon atom in their molecules so that there are two optical isomers. These are also included with the scope of the invention.

Practical embodiments for preparation of the amide compound (I) are shown in the following Examples.

EXAMPLE 1

(Compound No. 1)

To a solution of imidazole (2.72 g; 40 mmol) in dry tetrahydrofuran (60 ml) was added dropwise thionyl chloride (1.20 g; 10 mmol) under ice-cooling while stirring. After the resultant mixture was turned to room temperature, 2,4-dimethyl-5-thiazolecarboxylic acid (1.57 g; 10 mmol) was added thereto at once, and stirring was continued for 30 minutes, whereby 5-imidazolylcarbonyl-2,4-dimethylthiazole was produced. To the mixture was added dropwise a solution of 2-(2-furyl)aminoacetonitrile (1.46 g; 12 mmol) in dry tetrahydrofuran under ice-cooling, and the resultant mixture was stirred at room temperature for 1 hour. After completion of the reaction, tetrahydrofuran was removed under reduced pressure to separate the residue. Water was added to the residue, which was extracted with ethyl acetate. The ethyl acetate layer was washed twice with water, dried over anhydrous magnesium sulfate and concentrated under reduced pressure to give crude crystals. Recrystallization from ethanol gave 2.0 g of 2-(2,4-dimethylthiazole-5-carboxamido)-2-(2-furyl)acetonitrile as colorless crystals. m.p., 108°–109° C. Yield, 74%.

EXAMPLE 2

(Compound No. 2)

To a solution of 2-(3-furyl)aminoacetonitrile (1.46 g; 12 mmol) and triethylamine (1.20 g; 12 mmol) in tetrahydrofuran (30 ml) was added slowly a solution of 2,4- dimethylthiazole-5-carbonyl chloride (1.75 g; 10 mmol) in tetrahydrofuran (10 ml) with ice-cooling. After the addition, the mixture was turned to room temperature and stirring was continued for 3 hours. The solvent was removed under reduced pressure to separate the residue. Water was added to the residue, which was extracted with ethyl acetate. The ethyl acetate layer was washed with water and dried over anhydrous magnesium sulfate and concentrated under reduced pressure to give crude oil. The oil was purified by silica-gel column chromatography (eluent:n-hexane:ethyl acetate=2:1 by volume) to give 1.93 g of 2-(2,4-dimethylthiazole-5-carboxamido)-2-(3-furyl)acetonitrile as colorless crystals. m.p., 94°-96° C. Yield, 74%.

EXAMPLE 3

(Compound No. 3)

To a solution of imidazole (2.27 g; 40 mmol) in dry tetrahydrofuran (60 ml) was added dropwise thionyl chloride (1.20 g; 10 mmol) under ice-cooling while stirring. After the resultant mixture was turned to room temperature, 2,4-dimethyl-5-thiazolecarboxylic acid (1.57 g; 10 mmol) was added thereto at once, and stirring was continued for 30 minutes. To the mixture was added dropwise a solution of 2-(2-thienyl)aminoacetonitrile (1.65 g; 12 mmol) in dry tetrahydrofuran under ice-cooling, and the resultant mixture was stirred at room temperature for 1 hour. After completion of the reaction, tetrahydrofuran was removed under reduced pressure to separate the residue. Water was added to the residue, which was extracted with ethyl acetate. The ethyl acetate layer was washed with water, dried over anhydrous magnesium sulfate and concentrated under reduced pressure to give crude oil. The oil was purified by silica-gel column chromatography (eluent:n-hexane:ethyl acetate=2:1 volume) to give crude crystals. Recrystallization from n-hexane/ethyl acetate gave 1.80 g of 2-(2,4-dimethylthiazole-5-carboxamido)-2-(2-thienyl)acetonitrile as colorless crystals. m.p., 127.5°-128.5° C. Yield, 65%.

EXAMPLE 4

(Compound No. 4)

To a solution of imidazole (2.72 g; 40 mmol) in dry tetrahydrofuran (60 ml) was added dropwise thionyl chloride (1.20 g; 10 mmol) under ice-cooling while stirring. After the resultant mixture was turned to room temperature, 2,4-dimethyl-5-thiazolecarboxylic acid (1.57 g; 10 mmol) was added thereto at once, and stirring was continued for 30 minutes. To the mixture was added dropwise a solution of 2-(3-thienyl)aminoacetonitrile (1.65 g; 12 mmol) in dry tetrahydrofuran under ice-cooling, and the resultant mixture was stirred at room temperature for 1 hour. After completion of the reaction, tetrahydrofuran was removed under reduced pressure to separate the residue. Water was added to the residue, which was extracted with ethyl acetate. The ethyl acetate layer was washed with water twice, dried over anhydrous magnesium sulfate and concentrated under reduced pressure to give crude oil. The oil was purified by silica-gel column chromatography (eluent:n-hexane:ethyl acetate=2:1 volume) to give crude crystals. Recrystallization from n-hexane/ethyl acetate gave 1.95 g of 2-(2,4-dimethylthiazole-5-carboxamido)-2-(3-thienyl)acetonitrile as colorless crystals. m.p., 94°-95° C. Yield, 70%.

EXAMPLE 5

(Compound No. 5)

To a solution of imidazole (2.72 g; 40 mmol) in dry tetrahydrofuran (60 ml) was added dropwise thionyl chloride (1.20 g; 10 mmol) under ice-cooling while stirring. After the resultant mixture was turned to room temperature, 2-methyl-4-ethyl-5-thiazolecarboxylic acid (1.71 g; 10 mmol) was added thereto at once, and stirring was continued for 30 minutes. To the mixture was added dropwise a solution of 2-(2-furyl)aminoacetonitrile (1.46 g; 12 mmol) in dry tetrahydrofuran under ice-cooling, and the resultant mixture was stirred at room temperature for 1 hour. After completion of the reaction, tetrahydrofuran was removed under reduced pressure to separate the residue. Water was added to the residue, which was extracted with ethyl acetate. The ethyl acetate layer was washed with water twice, dried over anhydrous magnesium sulfate and concentrated under reduced pressure to give crude oil. The oil was purified by silica-gel column chromatography (eluent:n-hexane:ethyl acetate=2:1 volume) to give crude crystals. Recrystallization from n-hexane/ethyl acetate gave 1.58 g of 2-(2-methyl-4-ethylthiazole-5-carboxamido)-2-(2-furyl)acetonitrile as colorless crystals. m.p., 125°-126° C. Yield, 57%.

EXAMPLE 6

(Compound No. 6)

To a solution of imidazole (2.72 g; 40 mmol) in dry tetrahydrofuran (60 ml) was added dropwise thionyl chloride (1.20 g; 10 mmol) under ice-cooling while stirring. After the resultant mixture was turned to room temperature, 2-methyl-4-ethyl-5-thiazolecarboxylic acid (1.65 g; 10 mmol) was added thereto at once, and stirring was continued for 30 minutes. To the mixture was added dropwise a solution of 2-(2-thienyl)aminoacetonitrile (1.65 g; 12 mmol) in dry tetrahydrofuran under ice-cooling, and the resultant mixture was stirred at room temperature for 1 hour. After completion of the reaction, tetrahydrofuran was removed under reduced pressure to separate the residue. Water was added to the residue, which was extracted with ethyl acetate. The ethyl acetate layer was washed with water twice, dried over anhydrous magnesium sulfate and concentrated under reduced pressure to give crude oil. The oil was purified by silica-gel column chromatography (eluent:n-hexane:ethyl acetate=2:1 volume) to give crude crystals. Recrystallization from n-hexane/ethyl acetate gave 1.74 g of 2-(2-methyl-4-ethylthiazole-5-carboxamido)-2-(2-thienyl)acetonitrile as colorless crystals. m.p., 137°-138° C. Yield, 60%.

EXAMPLE 7

(Compound No. 7)

To a solution of imidazole (2.72 g; 40 mmol) in dry tetrahydrofuran (60 ml) was added dropwise thionyl chloride (1.20 g; 10 mmol) under ice-cooling while stirring. After the resultant mixture was turned to room temperature, 2-methyl-4-n-propyl-5-thiazolecarboxylic acid (1.85 g; 10 mmol) was added thereto at once, and stirring was continued for 1 hour. To the mixture was added dropwise a solution of 2-(2-thienyl)aminoacetonitrile (1.65 g; 12 mmol) in dry tetrahydrofuran under ice-cooling, and the resultant mixture was stirred at room temperature for 3 hours. After completion of the reaction, tetrahydrofuran was removed under reduced pressure to separate the residue. Water was added to the residue, which was extracted with ethyl acetate. The ethyl acetate layer was washed with water twice, dried over anhydrous magnesium sulfate and concentrated under reduced pressure to give crude oil. The oil was purified by silica-gel column chromatography (eluent:n-hexane:ethyl acetate=2:1 volume) to give crude crystals. Recrystallization from n-hexane/ethyl acetate gave 1.61 g of 2-(2-methyl-4-n-propylthiazole-5-carboxamido)-2-(2-thienyl)acetonitrile as colorless crystals. m.p., 125°–126° C. Yield, 53%.

EXAMPLE 8

(Compound No. 9)

To a solution of imidazole (2.72 g; 40 mmol) in dry tetrahydrofuran (60 ml) was added dropwise thionyl chloride (1.20 g; 10 mmol) under ice-cooling while stirring. After the resultant mixture was turned to room temperature, 2-methyl-4-isopropyl-5-thiazolecarboxylic acid (1.85 g; 10 mmol) was added thereto at once, and stirring was continued for 1 hour. To the mixture was added dropwise a solution of 2-(2-thienyl)aminoacetonitrile (1.65 g; 12 mmol) in dry tetrahydrofuran under ice-cooling, and the resultant mixture was stirred at room temperature for 3 hours. After completion of the reaction, tetrahydrofuran was removed under reduced pressure to separate the residue. Water was added to the residue, which was extracted with ethyl acetate. The ethyl acetate layer was washed with water twice, dried over anhydrous magnesium sulfate and concentrated under reduced pressure to give crude oil. The oil was purified by silica-gel column chromatography (eluent:n-hexane:ethyl acetate=2:1 volume) to give 1.49 g of 2-(2-methyl-4-isopropylthiazole-5-carboxamido)-2-(2-thienyl)acetonitrile as a viscous oil. $^1$H-NMR δ (CDCl$_3$): 1.26 (6H, d, J=6 Hz), 2.62 (3H, s), 3.70 (1H, sep, J=6 Hz), 6.35 (1H, d, J=8 Hz), 6.8–7.1 (4H, m). Yield, 49%.

In the same manner as above, the amide compounds (I) as shown in Table 1 are obtained.

TABLE 1

| Compound No | R$^1$ | R$^2$ | R$^3$ | Physical Property |
|---|---|---|---|---|
| 1 | Methyl | Methyl | 2-Furyl | m.p., 108–109° C. |
| 2 | Methyl | Methyl | 3-Furyl | m.p., 94–96° C. |
| 3 | Methyl | Methyl | 2-Thienyl | m.p., 127.5–128.5° C. |
| 4 | Methyl | Methyl | 3-Theinyl | m.p., 94–95° C. |
| 5 | Methyl | Ethyl | 2-Furyl | m.p., 125–126° C. |
| 6 | Methyl | Ethyl | 2-Thienyl | m.p., 137–138° C. |
| 7 | Methyl | n-Propyl | 2-Thienyl | m.p., 125–126° C. |
| 8 | Methyl | n-Propyl | 2-Furyl | m.p., 122–123° C. |
| 9 | Methyl | Isopropyl | 2-Thienyl | $^1$H-NMR δ (CDCl$_3$): 1.26 (6H, d, J = 6 Hz), 2.62 (3H, s), 3.70 (1H, sep, J = 6Hz), 6.35 (1H, d, J = 8 Hz), 6.8–7.1 (4H, m) |
| 10 | Ethyl | Methyl | 2-Thienyl | m.p., 100–101° C. |
| 11 | Ethyl | Ethyl | 2-Thienyl | m.p., 129–130° C. |
| 12 | H | Ethyl | 2-Thienyl | m.p., 130–131° C. |
| 13 | H | Ethyl | 2-Furyl | m.p., 102–103° C. |
| 14 | Methyl | Ethyl | 3-Thienyl | m.p., 115–116° C. |

For the practical use of the amide compounds (I) as fungicides, they may be applied as such or in preparation forms such as emulsifiable concentrates, wettable powders, suspensions, powders or granules. Such preparation forms can be formulated in a per se conventional manner, e.g. by mixing at least one of the amide compounds (I) with an appropriate solid or liquid carrier(s) or diluent(s) and, if necessary, an appropriate adjuvant(s) (e.g. surfactants, adherents, dispersants, stabilizers) for improving the dispersibility and other properties of the active ingredient.

Examples of the solid carriers or diluents are fine powders or granules of kaolin clay, attapulgite clay, bentonite, acid clay, pyrophyllite, talc, diatomaceous earth, calcite, corn rachis powders, walnut powders, urea, ammonium sulfate, synthetic hydrated silica, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, acetonitrile, water, etc.

The surface active agent used for emulsification, dispersion or spreading may be any of the anionic and non-ionic type of agents. Examples of the surface active agent include anionic surfactants and non-ionic surfactans such as alkysulfates, alkylarylsulfonates, dialkylsulfosuccinates, phosphates of polyoxyethylenealkylaryl ethers, condensates of naphthalenesulfonic acid and formalin, polyoxyethylene alkyl ethers, polyoxyethylene polyoxypropylene block copolymers, sorbitan fatty acid esters and polyoxyethylene sorbitan fatty acid esters. Examples of the auxiliary agents include ligninsulfonates, sodium alginate, polyvinyl alcohol, gum arabic, CMC (carboxymethyl cellulose), PAP (isopropyl acid phosphate), etc.

For the purpose of producing the fungicidal effect, the amide compounds (I) may be generally used in a range of about 0.01 to 50 grams, preferably about 0.05 to 10 grams, per are. In general, the concentration of the active ingredient in the fungicidal composition of the invention may be from about 0.01 to 99.9% by weight, preferably from about 1 to 90% by weight. For the practical use, the composition in the preparation form as above exemplified is diluted usually with water to make a concentration of about 0.0001 to 0.5% by weight, preferably about 0.0005 to 0.2% by weight, of the active ingredient, and then the resultant dilution is applied. When, however, the composition is formulated in dusts or granules, it is normally applied as such without dilution.

It is also notable that the amide compounds (I) may be used in admixture with other fungicides to enhance their fungicidal activity. Further, they may be applied in association with insecticides, miticides, nematocides, herbicides, plant-growth regulators, fertilizers, etc.

As stated above, the amide compounds (I) show appreciable fungicidal property. For instance, they exert preventive, curative and systemic effect against a wide variety of plant diseases caused by phytopathogenic fungi, of which typical examples are as follows: downy mildew of vegetables or radish (*Peronospora brassicae*), spinaches (*Peronospora spinaciae*), tobacco (*Peronospora tabacina*), cucumber (*Pseudoperonospora cubensis*), grapes (*Plasmopara viticola*) or parsley (*Plasmopara nivea*), blight of apple, strawberry or ginseng (*Phytophthora cactorum*), tomato or cucumber (*Phytophthora capsici*), pineapple (*Phytophthora cinnamomi*), potato, tomato or eggplant (*Phytophthora infestans*) or tobacco, horse beans or onion (*Phytophthora nicotianae* var. *nicotianae*), damping-off of spinach (*Phythium* sp.) or cucumber (*Pythium aphanidermatum*), browning root rot of wheats (*Phytium* sp.), damping-off of tobacco seedlings (*Pythium debaryanum*), Phythium rot of soybeans (*Phythium aphanidermatum, P. debaryanum, P. irregulare, P. myiotylum, P. ultimam*), etc.

Some practical embodiments of the fungicidal composition according to the invention are illustratively shown in the following Formulation Examples wherein part(s) are by weight.

FORMULATION EXAMPLE 1

Fifty parts of each of Compound Nos. 1 to 14, 3 parts of calcium ligninsulfonate, 2 parts of sodium laurylsulfonate and 45 parts of synthetic hydrated silica are mixed and thoroughly pulverized to obtain a wettable powder.

FORMULATION EXAMPLE 2

Twenty-five parts of each of Compound Nos. 1 to 14, 3 parts of polyoxyethylene sorbitan monooleate, 3 parts of CMC and 69 parts of water are mixed and thoroughly pulverized until the particle size of the active ingredient becomes less than 5 microns to obtain a suspension.

FORMULATION EXAMPLE 3

Two parts of each of Compound Nos. 1 to 14, 88 parts of kaolin clay and 10 parts of talc are mixed and thoroughly pulverized to obtain powders.

FORMULATION EXAMPLE 4

Twenty parts of each of Compound Nos. 1 to 14, 14 parts of polyoxyethylene styrylphenyl ether, 6 parts of calcium dodecylbenzenesulfonate and 60 parts of xylene are mixed together to obtain an emulsifiable concentrate.

FORMULATION EXAMPLE 5

Two parts of each of Compound Nos. 1 to 14, 1 part of synthetic hydrated silica, 2 parts of calcium ligninsulfonate, 30 parts of bentonite and 65 parts of kaolin clay are mixed and thoroughly pulverized with addition of water to obtain granules.

Typical test data indicating the excellent fungicidal activity of the amide compounds (I) are shown below. The assessment data are converted to percent disease control. 100% means no infection; 0% means that the plant are totally infected compared with the control plant.

The compounds as shown in Table 2 were used for comparison:

TABLE 2

| Compound No. | Structure | Remarks |
|---|---|---|
| A | Cl-C6H3(Cl)-CONH-CH(CN)-furan | U.S. Pat. No. 4,432,784 |
| B | Cl-C6H4-CONH-CH(CN)-furan | U.S. Pat. No. 4,432,784 |

TABLE 2-continued

| Compound No. | Structure | Remarks |
|---|---|---|
| C | Cl-C6H3(Cl)-CONH-CH(CN)-pyrazole | U.S. Pat. No. 4,515,959 |
| D | (H3C)2-C6H3-CONH-CH(CN)-pyrazole | U.S. Pat. No. 4,515,959 |
| E | furan-CONH-CH(CN)-furan | U.S. Pat. No. 4,432,784 |
| F | 1,3-dimethylpyrazole-CONH-CH(CN)-thiophene | Japanese Pat. Appln. No. 181743/87 |

TEST EXAMPLE 1

Preventive Effect on Late Blight of Potatoes (*Phytophthora infestans*):

A plastic pot was filled with sandy soil, and potatoes (var: Danshaku) were sowed therein, followed by cultivation in a greenhouse for 40 days. The test compound formulated in a wettable powder according to Formulation Example 1 and diluted with water to a prescribed concentration was thoroughly sprayed over the seedlings of the test plants, and a spore suspension of *Phytophthora infestants* was inoculated by spreading over the test plants, which were allowed to stand at 20° C. overnight under a humid condition. The test plants were further grown for 5 days under illumination and observed. The results are shown in Table 3.

TEST EXAMPLE 2

Curative Effect on Late Blight of Potatoes (*Phytophthora infestans*):

A plastic pot was filled with sandy soil, and potatoes (var: Danshaku) were sowed therein, followed by cultivation in a greenhouse for 40 days. A spore suspension of *Phytophthora infestans* was inoculated by spreading over the seedlings of the test plants, which were then allowed to stand at 20° C. overnight under a humid condition. The test compound formulated in a wettable powder according to Formulation Example 1 and diluted with water to a prescribed concentration was thoroughly sprayed over the test plants, which were further grown for 5 days under illumination and observed. The results are shown in Table 3.

TEST EXAMPLE 3

Preventive Effect on Late Blight of Tomato (*Phytophthora infestans*):

A plastic pot was filled with sandy soil, and seeds of tomato (var: Ponte Rosa) were sowed therein, followed by cultivation in a greenhouse for 20 days. The test compound formulated in a wettable powder according to Formulation Example 1 and diluted with water to a prescribed concentration was thoroughly sprayed over the seedlings at the 2 to 3 leaf-stage of the test plants, and a spore suspension of *Phytophthora infestans* was inoculated by spreading over the test plants, which were allowed to stand at 20° C. overnight under a humid condition. The test plants were further grown for 5 days under illumination and observed. The results are shown in Table 3.

TEST EXAMPLE 4

Curative Effect on Late Blight of Tomato (*Phytophthora infestans*):

A plastic pot was filled with sandy soil, and seeds of tomato (var: Ponte Rosa) were sowed therein, followed by cultivation in a greenhouse for 20 days. A spore suspension of *Phytophthora infestans* was inoculated by spreading over the seedlings at the 2 to 3 leaf-stage of the test plants, which were then allowed to stand at 20° C. overnight under a humid condition. The test compound formulated in a wettable powder according to Formulation Example 1 and diluted with water to a prescribed concentration was thoroughly sprayed over the test plants, which were further grown for 5 days under illumination and observed. The results are shown in Table 3.

TEST EXAMPLE 5

Preventive Effect on Downy Mildew of Grapes (*Plasmopara viticola*):

A plastic pot was filled with sandy soil, and seeds of grapes (var: Berry-A) were sowed therein, followed by cultivation in a greenhouse for 50 days. The test compound formulated in a wettable powder according to Formulation Example 1 and diluted with water to a prescribed concentration was thoroughly sprayed over the seedlings at the 6 to 7 leaf-stage of the test plants, and a spore suspension of *Plasmopara viticola* was inoculated by spreading over the test plants, which were allowed to stand at 20° C. overnight under a humid condition. The test plants were further grown for 8 days under illumination and observed. The results are shown in Table 3.

TEST EXAMPLE 6

Curative Effect on Downy Mildew of Grapes (*Plasmopara viticola*):

A plastic pot was filled with sandy soil, and seeds of grapes (var: Barry-A) were sowed therein, followed by cultivation in a greenhouse for 50 days. A spore suspension of *Plasmopara viticola* was inoculated by spreading over the seedlings at the 6 to 7 leaf-stage of the test plants, which were then allowed to stand at 20° C. overnight under a humid condition. The test compound formulated in a wettable powder according to Formulation Example 1 and diluted with water to a prescribed concentration was thoroughly sprayed over the test plants, which were further grown for 8 days under illumination and observed. The results are shown in Table 3.

TEST EXAMPLE 7

Preventive Effect on Downy Mildew of Cucumber (*Pseudoperonospora cubensis*):

A plastic pot was filled with sandy soil, and seeds of cucumber (var: Sagamihanjiro) were sowed therein, followed by cultivation in a greenhouse for 14 days. The test compound formulated in a wettable powder according to Formulation Example 1 and diluted with water to a prescribed concentration was thoroughly sprayed over the seedlings of the test plants, and a spore suspension of *Pseudoperonospora cubensis* was inoculated by spreading over the test plants, which were allowed to stand at 20° C. overnight under a humid condition. The test plants were further grown for 5 days under illumination and observed. The results are shown in Table 3.

TEST EXAMPLE 8

Curative Effect on Downy Mildew of Cucumber (*Pseudoperonospora cubensis*):

A plastic pot was filled with sandy soil, and seeds of cucumber (var: Sagamihanjiro) were sowed therein, followed by cultivation in a greenhouse for 14 days. A spore suspension of *Pseudoperonospora cubensis* was inoculated by spreading over the seedlings of the test plants, which were then allowed to stand at 20° C. overnight under a humid condition. The test compound formulated in a wettable powder according to Formulation Example 1 and diluted with water to a prescribed concentration was thoroughly sprayed over the test plants, which were further grown for 8 days under illumination and observed. The results are shown in Table 3.

TABLE 3

| Compound No. | Concentration (ppm) | Potato Preventive effect | Potato Curative effect | Tomato Preventive effect | Tomato Curative effect | Grape Preventive effect | Grape Curative effect | Cucumber Preventive effect | Cucumber Curative effect |
|---|---|---|---|---|---|---|---|---|---|
| 1 | 100 | 100 | 100 | 100 | 100 | 100 | 100 | 100 | 100 |
|   | 50 | 75 | 70 | 80 | 70 | 75 | 70 | 85 | 80 |
| 2 | 100 | 100 | 100 | 100 | 100 | 100 | 100 | 100 | 100 |
|   | 50 | 75 | 70 | 75 | 70 | 75 | 70 | 80 | 80 |
| 3 | 100 | 100 | 100 | 100 | 100 | 100 | 100 | 100 | 100 |
|   | 50 | 80 | 80 | 80 | 80 | 80 | 80 | 90 | 90 |
| 4 | 100 | 100 | 100 | 100 | 100 | 100 | 100 | 100 | 100 |
|   | 50 | 80 | 80 | 80 | 80 | 80 | 80 | 90 | 90 |
| 5 | 100 | 100 | 100 | 100 | 100 | 100 | 100 | 100 | 100 |
|   | 50 | 100 | 75 | 100 | 70 | 100 | 70 | 80 | 80 |
| 6 | 100 | 100 | 100 | 100 | 100 | 100 | 100 | 100 | 100 |
|   | 50 | 100 | 100 | 100 | 100 | 100 | 100 | 100 | 100 |
| 7 | 100 | 100 | — | 100 | — | 100 | — | 100 | — |
|   | 50 | 70 | — | 70 | — | 70 | — | 80 | — |

TABLE 3-continued

| Compound No. | Concentration (ppm) | Potato | | Tomato | | Grape | | Cucumber | |
|---|---|---|---|---|---|---|---|---|---|
| | | Preventive effect | Curative effect | Preventive effect | Curative effect | Preventive effect | Curative effect | Preventive effect | Curative effect |
| 8 | 100 | 100 | — | 100 | — | 100 | — | 100 | — |
| | 50 | 70 | — | 70 | — | 70 | — | 80 | — |
| 9 | 100 | 100 | — | 100 | — | 100 | — | 100 | — |
| | 50 | — | — | — | — | — | — | — | — |
| 10 | 100 | 100 | — | 100 | — | 100 | — | 100 | — |
| | 50 | 70 | — | 70 | — | 70 | — | 80 | — |
| 11 | 100 | 100 | — | 100 | — | 100 | — | 100 | — |
| | 50 | 70 | — | 70 | — | 70 | — | 80 | — |
| 14 | 100 | 100 | 100 | 100 | 100 | 100 | 100 | 100 | 100 |
| | 50 | 100 | 100 | 100 | 100 | 100 | 100 | 100 | 100 |
| A | 100 | 0 | 0 | 0 | 0 | 0 | 0 | 0 | 0 |
| B | 100 | 0 | 0 | 0 | 0 | 0 | 0 | 0 | 0 |
| C | 100 | 15 | 0 | 20 | 0 | 10 | 0 | 20 | 0 |
| D | 100 | 15 | 0 | 20 | 0 | 10 | 0 | 20 | 0 |
| E | 100 | 0 | 0 | 0 | 0 | 0 | 0 | 0 | 0 |
| F | 100 | 100 | 100 | 100 | 100 | 100 | 100 | 100 | 100 |
| | 50 | 70 | 70 | 75 | 70 | 70 | 70 | 75 | 75 |

TEST EXAMPLE 9

Soil Drench Test on Late Blight of Tomato (*Phytophthora infestans*):

A plastic pot was filled with sandy soil, and seeds of tomato (var: Ponte Rosa) were sowed therein, followed by cultivation in a greenhouse for 20 days. When the seedlings have grown to the 2 to 3-leaf stage, the test compound formulated in an emulsifiable concentrate according to Formulation Example 4 and diluted with water to a prescribed concentration was poured into the soil, and the test plants were allowed to stand in the greenhouse overnight. A spore suspension of *Phytophthora infestants* was inoculated by spreading over the test plants, which were allowed to stand at 20° C. overnight under a humid condition. The test plants were further grown for 5 days under illumination and subjected to observation for the preventive effect. The results are shown in Table 4.

TABLE 4

| Compound No. | Concentration (g/a) | Preventive effect |
|---|---|---|
| 1 | 10 | 100 |
| 2 | 10 | 100 |
| 3 | 10 | 100 |
| 4 | 10 | 100 |
| 5 | 10 | 100 |
| 6 | 10 | 100 |
| 14 | 10 | 100 |
| A | 100 | 0 |
| B | 100 | 40 |
| E | 100 | 45 |

TEST EXAMPLE 10

Phytotoxicity:

Over the seedlings of grapes (var: Berry-A), tomato (var: Ponte Rosa) and cucumber (var: Sagamihanjiro), the test compound formulated in a wettable powder according to Formulation Example 1 and diluted with water to a prescribed concentration was sprayed, and the test plants were further grown in a greenhouse for 2 weeks and subjected to observation for the phytotoxicity to the test plants. The phytotoxicity was visually observed and rated as 0, 1, 2, 3, 4 or 5 depending upon the degree of damage wherein 5 indicates no growth of the plants due to severe phytotoxicity whereas 0 indicates no phytotoxicity. The results are shown in Table 5.

TABLE 5

| Compound No. | Concentration of active ingredient (ppm) | Phytotoxicity | | |
|---|---|---|---|---|
| | | Tomato | Grape | Cucumber |
| 1 | 1000 | 0 | 0 | 0 |
| 2 | 1000 | 0 | 0 | 0 |
| 3 | 1000 | 0 | 0 | 0 |
| 4 | 1000 | 0 | 0 | 0 |
| 5 | 1000 | 0 | 0 | 0 |
| 6 | 1000 | 0 | 0 | 0 |
| 7 | 1000 | 0 | 0 | 0 |
| 8 | 1000 | 0 | 0 | 0 |
| 9 | 1000 | 0 | 0 | 0 |
| 10 | 1000 | 0 | 0 | 0 |
| 11 | 1000 | 0 | 0 | 0 |
| 14 | 1000 | 0 | 0 | 0 |
| A | 1000 | 5 | 4 | 4 |
| | 500 | 4 | 3 | 3 |
| B | 1000 | 5 | 4 | 4 |
| | 500 | 4 | 3 | 3 |
| C | 500 | 5 | 5 | 5 |
| F | 1000 | 4 | 3 | 4 |
| | 500 | 3 | 2 | 3 |

What is claimed is:

1. An amide compound of the formula:

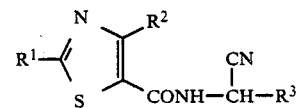

wherein $R^1$ and $R^2$ are, the same or different, each a hydrogen atom or a $C_1$-$C_3$ alkyl group and $R^3$ is a 2-furyl group, a 3-furyl group, a 2-thienyl group or a 3-thienyl group.

2. The amide compound according to claim 1, which is in an optically active form.

3. The amide compound according to claim 1, wherein $R^1$ is a methyl group, $R^2$ is a methyl group or an ethyl group and $R^3$ is a 2-thienyl group or a 3-thienyl group.

4. The amide compound according to claim 1, wherein $R^1$ is a methyl group, $R^2$ is an ethyl group and $R^3$ is a 2-thienyl group or a 3-thienyl group.

5. A fungicidal composition which comprises as an active ingredient a fungicidally effective amount of an amide compound of the formula:

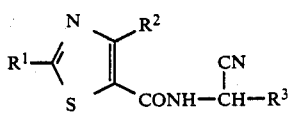

wherein $R^1$ and $R^2$ are, the same or different, each a hydrogen atom or a $C_1$–$C_3$ alkyl group and $R^3$ is a 2-furyl group, a 3-furyl group, a 2-thienyl group or a 3-thienyl group, and an inert carrier or diluent.

6. A method for controlling phytopathogenic fungi which comprises applying a fungicidally effective amount of an amide compound of the formula:

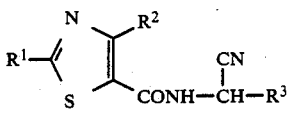

wherein $R^1$ and $R^2$ are, the same or different, each a hydrogen atom or a $C_1$–$C_3$ alkyl group and $R^3$ is a 2-furyl group, a 3-furyl group, a 2-thienyl group or a 3-thienyl group.

7. The amide compound according to claim 1, wherein $R^1$ is a methyl group, $R^2$ is a methyl group and $R^3$ is a 2-furyl group.

8. The amide compound according to claim 1, wherein $R^1$ is a methyl group, $R^2$ is a methyl group and $R^3$ is a 3-furyl group.

9. The amide compound according to claim 1, wherein $R^1$ is a methyl group, $R^2$ is a methyl group and $R^3$ is a 2-thienyl group.

10. The amide compound according to claim 1, wherein $R^1$ is a methyl group, $R^2$ is a methyl group and $R^3$ is a 3-thienyl group.

11. The amide compound according to claim 1, wherein $R^1$ is a methyl group, $R^2$ is an ethyl group and $R^3$ is a 2-furyl group.

12. The amide compound according to claim 1, wherein $R^1$ is a methyl group, $R^2$ is an ethyl group and $R^3$ is a 2-thienyl group.

13. The amide compound according to claim 1, wherein $R^1$ is a methyl group, $R^2$ is an ethyl group and $R^3$ is a 3-thienyl group.

* * * * *